United States Patent [19]
Winterton et al.

[11] Patent Number: 5,882,348
[45] Date of Patent: Mar. 16, 1999

[54] VALVED MANIFOLD

[75] Inventors: Reed F. Winterton, Salt Lake City; Sean P. Hanson, Murray, both of Utah

[73] Assignee: Sorenson Critical Care, Inc., Salt Lake City, Utah

[21] Appl. No.: 792,067

[22] Filed: Feb. 3, 1997

[51] Int. Cl.⁶ .................................................. A61M 25/00
[52] U.S. Cl. ........................... 604/283; 604/248; 251/310
[58] Field of Search ................................. 604/30, 32, 246, 604/248, 280, 283; 251/142, 149, 205–209, 292, 304, 309–311, 352

[56] References Cited

U.S. PATENT DOCUMENTS

| | | | |
|---|---|---|---|
| 3,273,595 | 9/1966 | Novak | 251/310 X |
| 4,648,868 | 3/1987 | Hardwick et al. | 604/32 |
| 5,288,290 | 2/1994 | Brody | 604/32 |
| 5,372,158 | 12/1994 | Berfield | 137/217 |

*Primary Examiner*—Corrine M. McDermott
*Attorney, Agent, or Firm*—Trask, Britt & Rossa

[57] ABSTRACT

A manifold assembly useful in patient ventilation/aspiration systems includes a stop cock valve with a hollow stem and a transverse slot arranged to permit the stem to be rotated between open and closed positions. In both positions, a ventilating pathway is maintained through the slot and the stem between ventilator and patient connection ports of the manifold. In open position the stem provides a travel pathway for a catheter between the patient connection port and an access port of the manifold. In closed condition, the stem seals this travel pathway.

20 Claims, 3 Drawing Sheets

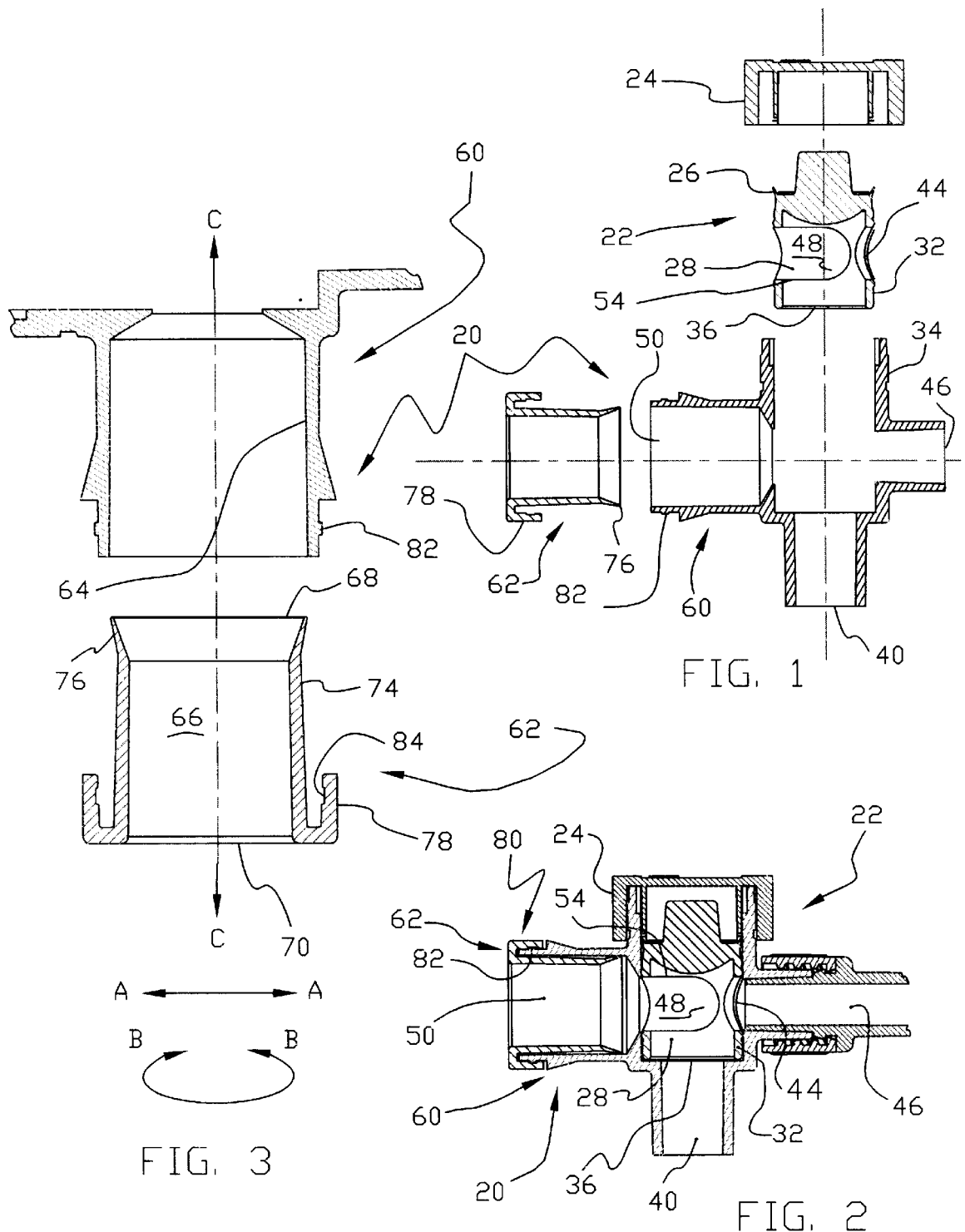

VALVED MANIFOLD

BACKGROUND OF THE INVENTION

1. Field

This invention relates generally to valved manifold devices, and is specifically directed to such devices in medical conduit systems. It provides a valved manifold particularly useful at the patient intubation interface of endotracheal ventilation/aspiration systems.

2. State of the Art

Many gas delivery systems, particularly in a hospital or laboratory environment, utilize manifold devices for directing fluid flow. There are a variety of circumstances in which it is necessary or desirable to provide multiple, yet isolated, other pathways through the interior of such a manifold. The manifold is often associated with other components as a system. When the individual components of such a system are subjected to mechanical forces tending to rotate one component with respect to another, it is often essential to provide that travel path through a joint structure which permits rotating or swiveling movement.

As an example, closed systems for endotracheal suctioning and ventilating typically include a manifold enabling introduction of ventilating gases and intermittent exhalation of patient breath simultaneously with insertion and operation of a tracheal suctioning catheter. The manifold structure typically includes multiple ports, usually the open ends of respective conduits extending from a common chamber. One such port is interfaced to a patient through a patient connection device. The suction catheter is often included within an assembly which is connectable to a second port of the manifold. The catheter assembly conventionally includes a collapsible plastic envelope positioned to entirely surround the catheter. A practitioner manually externally collapses the envelope onto the external surface of the catheter and advances the catheter through the manifold into an access tube connected to a patient, retracting the catheter in a similar fashion following the aspiration procedure.

The manifold thus provides a first pathway for ventilation gases and a second pathway for the catheter. The catheter provides isolation from the ventilating gases for fluids withdrawn from the patient through the manifold. When the catheter is withdrawn, it is often desired to continue regulated ventilation through the manifold. In some cases, it is desirable for the catheter assembly to be disconnected from the manifold without disturbing the ventilation of the patient. It is thus necessary to provide for a gas-tight sealing of the pathway formerly occupied by the catheter upon its removal. Previous efforts in this connection have involved the provision of auxiliary sealing structures for use in association with the manifold. These arrangements have had several disadvantages. Because they have not been integral with the manifold, their use has been inconvenient in practice. Certain resilient seals have been unacceptable because they lack the positive sealing characteristics of a mechanical valve. Available valves are not suitable for incorporation into a manifold because they lack the essential capability of providing a travel path for a catheter when catheter suction is needed. Any sealing arrangement employed should be as inexpensive as possible, thereby eliminating complex mechanical valve assemblies from practical consideration.

Manipulations, or other disturbances, of the catheter assembly tend to cause irritation to the patient and to impose strain on connection points within the assembly. These problems are alleviated to a considerable extent by the provision of a swivel capability (rotation about the longitudinal axis of the connection port) at the patient interface. Unfortunately, the provision of such a capability has heretofore involved the incorporation of swivel elements which are inordinately expensive and/or which provide an unreliable seal for the system.

Material prior art structures and methods are described, among other places, in U.S. Pat. Nos. 5,333,607 to Kee, et. al.; 5,354,267 to Niermann, et. al.; 5,357,946 and 5,445,141 to Kee, et. al. and 5,487,381 to Jinotti. These patents each disclose ventilator manifold devices and systems in which those devices are utilized.

The '267 patent, for example, discloses a manifold and a multi-position stop cock valve. The valve is provided with a "Tee" shaped internal stem channel pattern so that the stem may be positioned selectively to wash the internal lumen of a catheter, to irrigate the patient or to accommodate travel of the catheter through the stem to suction the patient. The valve may be plugged directly into an access port of the manifold. Patient ventilation is conducted without respect to the valve through other ports of the manifold. The valve itself constitutes an integral component of a catheter assembly and must be removed from the manifold with the remainder of that assembly.

There remains a need for an inexpensive, yet reliable, manifold assembly incorporating a valve positioned to minimize dead air space within the manifold and capable of passing a catheter. The valve must provide a sealed gas flow path through the manifold in both its open and closed conditions with respect to catheter travel. The manifold should further be removable from any associated catheter assembly. Ideally, the manifold should also include connection structure capable of providing a sealed passageway through a rotating or swiveling joint.

SUMMARY OF THE INVENTION

The invention may be embodied as a multi-function manifold positioned at the distal end of a catheter assembly. A catheter tube is slidable lengthwise through a passageway including ports at the proximal and distal sides of the manifold. A special valve is positioned within that passageway to minimize dead air space, and may be operated to open a travel path for the catheter through the manifold. The manifold preferably includes a patient connection conduit at its distal side for attachment to (and communication with) an indwelling intubation device, such as a tracheal tube, endotracheal tube or nasopharyngeal tube. The manifold also includes a ventilating structure extending radially from (and in fluid communication with) the passageway. The ventilating structure constitutes means for selectively introducing ambient air, oxygenated air and other therapeutic gases into the respiratory system of the patient. Other conduits may also be provided for the introduction of therapeutic and diagnostic implements and for the introduction of other suitable gases and lavage solutions to the respiratory system.

The manifold, and in particular, the manifold valve, is structured and arranged to enable simultaneous patient ventilation and protected tracheal suctioning. A suctioning catheter may be coupled at its proximal end to a suctioning valve. The distal end of the catheter may then be fed through a conduit at the proximal side of the manifold for reciprocal movement through the intubation device. The catheter is often provided in an assembly, whereby it is enveloped by a sterility-enhancing protective barrier, which is coupled to an access structure at the proximal side of the manifold. The manifold and valve may be integral with the catheter assembly, but are preferably detachable to facilitate multiple uses of the manifold, either in association with other assemblies or for other applications.

The manifold valve is structured and arranged as a stop cock with a specialized valve stem. The valve stem is fashioned to provide the previously described versatility of function to the manifold. The manifold may thus be positioned in a patient ventilating circuit in conventional fashion to function as a portion of that circuit. In that circumstance, the valve stem is positioned to maintain a first, ventilating, flow path through the manifold, including through a portion of the stem. As so positioned, the stem blocks flow through other selected travel paths within the manifold. In particular, the passageway required for the catheter, when it is present, is sealed against gas flow by the stem. The stem may be repositioned to permit passage of a catheter through a slot in the stem, while still maintaining the ventilation flow path in open condition.

A preferred valved manifold assembly includes a stop cock valve with a hollow stem and a transverse slot arranged to permit the stem to be rotated between open and closed positions. In both positions, a ventilating pathway is maintained through the stem between ventilator and patient connection ports of the manifold. In open position, the stem provides a travel pathway for a catheter between the patient connection port and an access port of the manifold. In closed condition, the stem seals this travel pathway. This structure is ideally suited for inclusion in patient ventilation/aspiration systems.

In summary, an interface assembly for closed system endotracheal ventilating and aspirating procedures may be embodied as a manifold having a ventilating port in open communication with an interior chamber, a patient connection port in open communication with the chamber and out of registration with the ventilation port and an access port in communication with the chamber and in registration with the patient connection port. The access port and patient connection ports are positioned to provide a catheter travel pathway through the access port, the chamber and the patient connection port. The assembly further includes a valve comprising a valve stem positioned within the catheter travel pathway. The stem is constructed and arranged for movement between first and second positions. In the first position, the stem blocks the pathway. In the second position, the stem provides a portion of the catheter travel pathway. Actuation structure is linked to the stem and manually operable to move the stem between the first and second positions. The valve is further constructed and arranged to avoid blocking gas flow between the ventilation port and the patient connection port.

In a typical embodiment, the ventilation port is oriented generally transverse the catheter travel pathway. The valve stem is ideally positioned within the interior chamber and is structured with a hollow center cavity opening towards the ventilation port. The hollow center is in open communication with the patient connection port, typically by means of a slot transverse the cavity and in registration with the patient connection port when the stem is in either the first or second position. The stem includes a wall with an outer surface in sealing relationship with the access port when the stem is in the first position. An opening through the wall into the cavity is positioned and configured to register with the access port when the stem is in the second position.

In use, the manifold assembly is interposed between an indwelling tube at the distal end of the manifold and a ventilating circuit. These junctions preferably embody a swivel configuration to permit left or right bedside placement of the ventilation circuitry and free rotation of the ventilation circuit with patient head movement to reduce the risk of extubation. Copending Ser. No. 08/794,337, identified in the internal files of the assignee and the attorney of record as Case No. 3097, describes an improved swivel connection apparatus which is generally useful for providing a gas-tight passageway between the interiors of discrete components of a fluid delivery system. The apparatus is structured and arranged to permit connection between tubular elements or conduits associated with such components. It is uniquely useful for connecting the manifold of this invention into endotracheal ventilating and aspirating assemblies. The disclosure of U.S. Ser. No. 08/794,337 is thus incorporated as a part of this disclosure, and certain preferred embodiments of the manifold of this invention incorporate such a connector.

The connector comprises a pair of cooperating parts. The first such part typically comprises a structural element carried by the manifold of the invention. This structural element may take a variety of forms, but in any case presents an approximately cylindrical interior surface, constituting the female portion of the connector.

The second part of the connector has a hollow interior between first and second open ends. The first such end constitutes the male portion of the connector. It includes an outer surface configured to register, in sliding seal relation, with the female portion of the connector. This outer surface is thus approximately cylindrical and is sized appropriately for insertion within the female portion. The distal end segment of the hollow cylinder (the male portion) is flared to an enlarged diameter so that it effects a self-biased engagement with the interior surface of the female portion across a relatively small surface area. In this fashion an effective gas seal is maintained with only a minor amount of frictional resistance against rotation of the male portion of the connector within the female portion of the connector. The flared segment is usually of reduced wall thickness and somewhat more flexible than the remainder of the male portion. The seal created by mating of the female and male portions is effective when the pressure within the hollow center of the connector is either positive or negative with respect to ambient conditions, within the practical range normally encountered in medical applications.

The second open end of the second part of the connector is structured and arranged for coupling to an intubation fixture. For example, a tube may be press fit into an entry port opening in the second end of the second part to effect a mechanical connection. Rotation of the tube then effects equivalent rotation of the male portion within the female portion of the connector, thereby avoiding strain in the joint between the system components. A terminal segment of the second end of the second part may further be structured cooperatively to form a journal bearing connection with the manifold. In this fashion, the first and second parts are supported against radial displacement or twist, which could interfere with smooth rotational displacement of these parts with respect to each other. In effect, approximately cylindrical male and female parts of the connector are adapted to couple by a plug fit (either a snap fit or press fit) connection, and those parts are structured to permit relative rotational displacement while they are in coupled condition.

BRIEF DESCRIPTION OF THE DRAWINGS

In the drawings, which illustrate what is currently regarded as the best mode for carrying out the invention:

FIG. 1 is an exploded view substantially in cross section of a valved manifold of this invention;

FIG. 2 is a substantially cross sectional view in elevation of the valved manifold of FIG. 1, in assembled condition;

FIG. 3 is an enlarged view in cross section of the connector portion of FIG. 1;

DETAILED DESCRIPTION OF THE ILLUSTRATED EMBODIMENT

Figure 4:
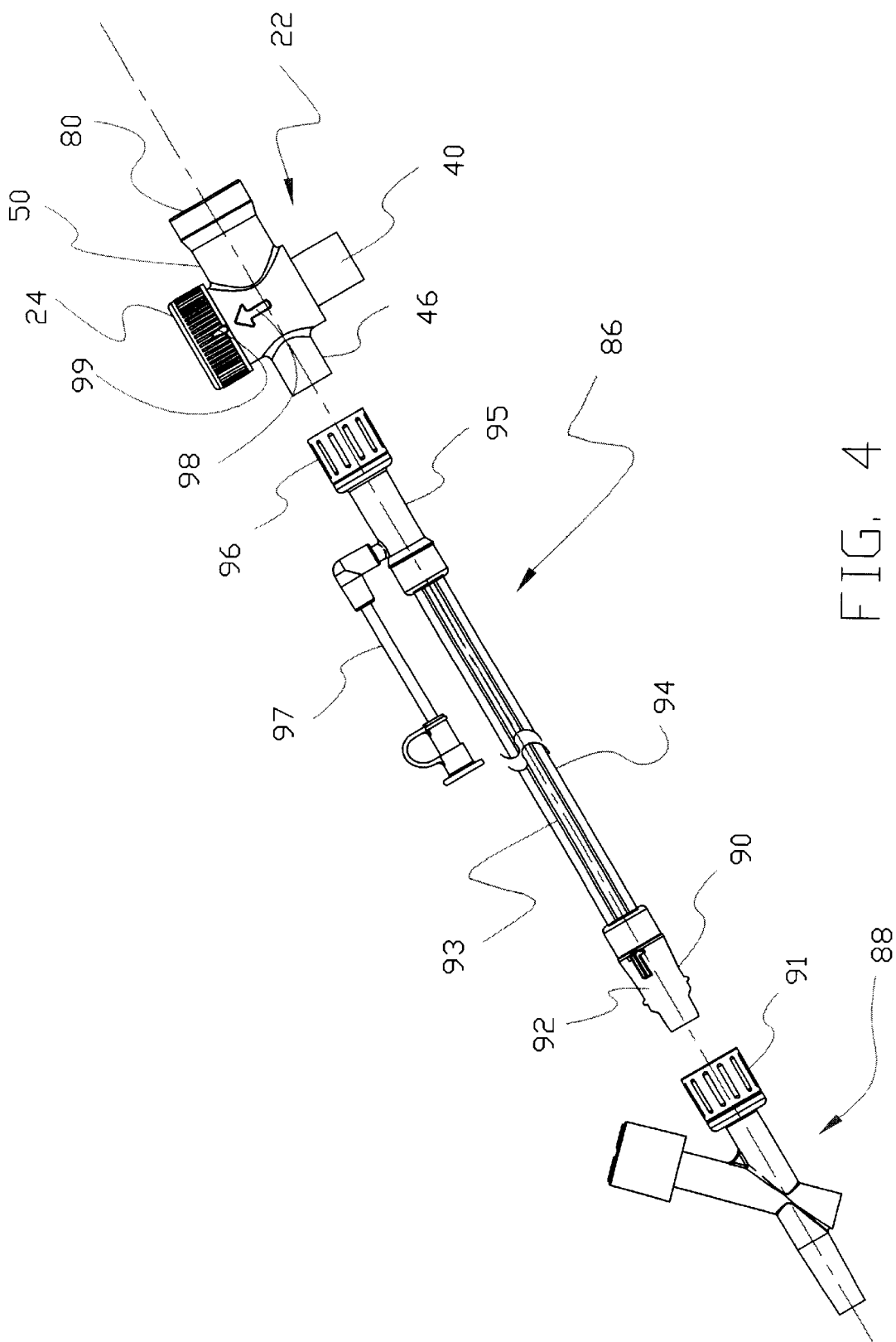
FIG. 4 is an exploded plan view, partially broken away, illustrating the manner in which the valved manifold of FIG. 1 may be connected in operable association with components of a suction catheter assembly.

The figures illustrate a preferred embodiment in which an optional swivel connector, designated generally 20, is fabricated as a portion of a stop cock manifold valve, designated generally 22. The valve 22 includes a knob 24, which may be turned by finger pressure to rotate a stem 26. The stem 26 is structured with an open interior 28, defined by a continuous wall 32. When the stem 26 is installed within the manifold body 34 of the valve, as shown by FIGS. 1 and 2, the open bottom 36 of the open interior 28 registers with a first manifold port 40.

The stem 26 may be rotated between a first, closed, position in which a solid portion 48 of the wall 32 is brought into registration with a second manifold port 46 and a second, open, position, as illustrated by FIGS. 1 and 2, wherein an opening 44 of the wall 32 registers with the second manifold port 46. In the second position, a travel path is opened between the second manifold port 46 and a third manifold port 50 through the open interior 28 of the stem 26. In the first position, the port 46 is sealed. In both positions of the stem 26, a transverse slot 54 through the continuous wall 32 provides a flow path between the port 50 and the open interior 28. Thus, in either position, the first manifold port 40 remains in open, fluid flow communication with the third manifold port 50 through the open bottom 36 of the open, the stem interior 28 and the slot 54.

The connector 20 comprises a pair of cooperating female and male parts, designated generally 60 and 62, respectively. The female part 60 is embodied as structure extending from the third manifold port 50. This structure 60 constitutes a connection conduit typical of manifold devices 20 of the type illustrated, and presents an approximately cylindrical interior surface 64, constituting the female portion of the connector 20.

The male part 62 of the connector 20 has a hollow interior 66 between first 68 and second 70 open ends The first end 68 constitutes the male portion of the connector. It includes an outer surface 74 configured to register, in sliding seal relation, with the female port 60 of the connector 20. This outer surface 74 is thus approximately cylindrical, and is sized appropriately for insertion within the female port 60. A distal end segment 74 is flared to an enlarged diameter so that it effects a self-biased engagement with the interior surface 64 of the female port 60 across an annular band of relatively small surface area. The flared segment 74 is of significantly reduced wall thickness, tapering towards the first end 68.

The second, open, end 70 of the male part 62 of the connector 20 is structured and arranged for coupling to a system component, such as an intubation tube (not shown). A terminal segment 76 of the second end 70 may further be structured cooperatively to form a journal bearing connection, designated generally 80 with structure 82 associated with the female part 60 of the connector 20, all as best shown by FIG. 3. The female 60 and second 62 parts are supported against radial displacement A—A or twist, which could interfere with smooth rotational displacement B—B of these parts with respect to each other. Specifically, in the illustrated instance, the structure 82 is formed as an annular ring which is received within a corresponding annular groove 84 comprising the terminal segment 76. These elements 82, 84 are structured and arranged to effect a fit snap fit connection which resists axial displacement C—C, but permits low resistance rotational displacement B—B, preferably over a full 360° range.

Figure 5:
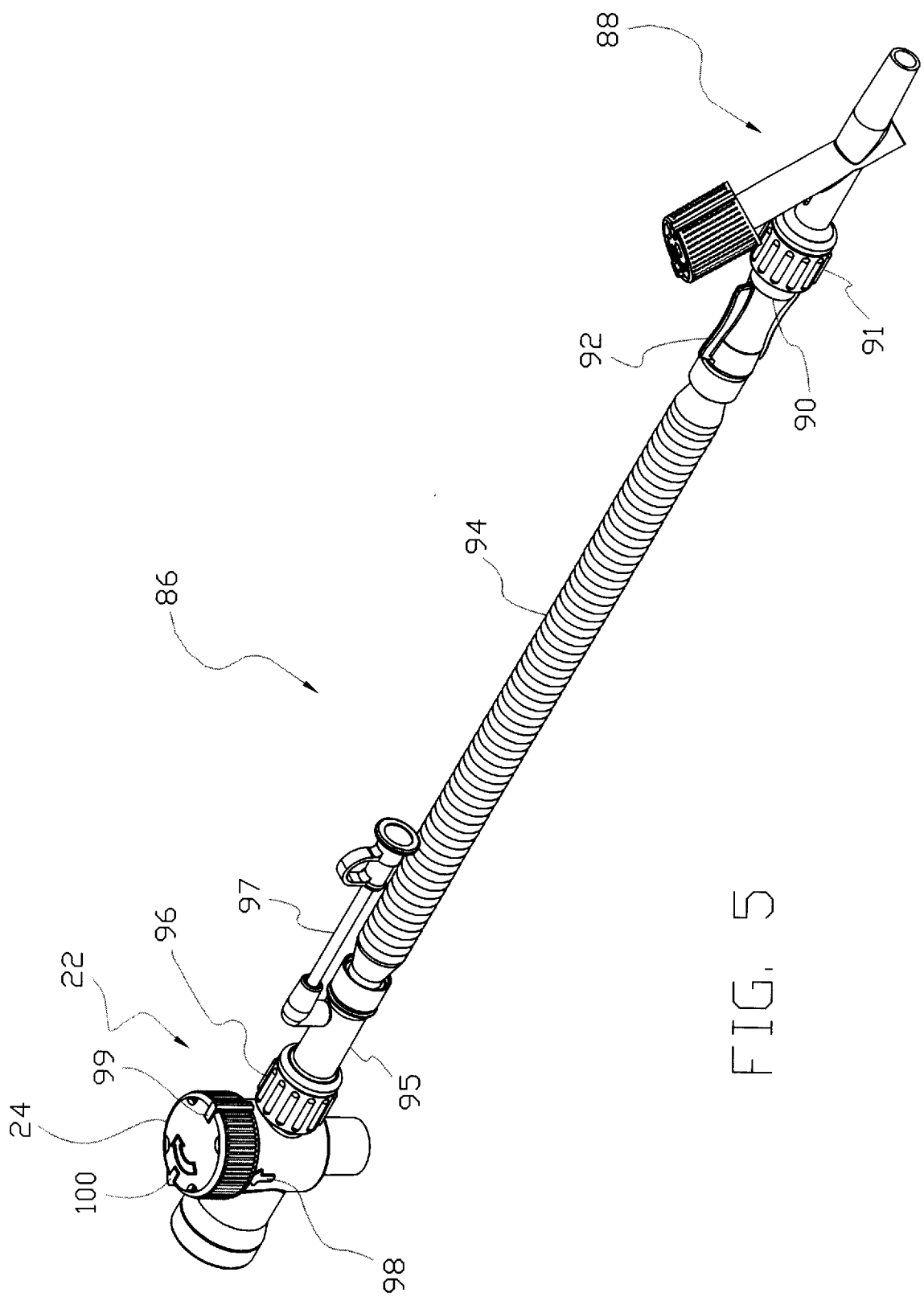
FIG. 5 is a perspective view of the assembly of FIG. 4, in fully assembled condition and rotated to expose features not visible in FIG. 4.

Referring to FIGS. 4 and 5, the manifold valve 22 is shown in association with a catheter assembly, designated generally 86. A suction control valve, generally 88, is connected to the proximal end 90 of the assembly 86 by means of a luer collar 91 and wing connector 92. A suction catheter 93 is carried within a flexible sheath 94, and may be selectively extended or withdrawn (by manual manipulation through the sheath) through a sputum trap 95, which is in turn connected by a luer collar 96 to the second manifold port 46 of the manifold 22. A swivel connector 80 is carried by the third connection port conduit 50. In the illustrated embodiment, first manifold port 40 constitutes a ventilation port, second manifold port 46 constitutes an access port for apparatus such as a suction catheter, and third manifold port 50 constitutes a patient connection port. An irrigation access tube 97 extends from the sputum trap 95. An arrow 98 registers with a witness mark 99 carried by the valve knob 24 to indicate the open/closed status of the valve 22. In its open condition, the catheter 93 may be manipulated through the valve 22 and the swivel connector 80 into a patient intubation fixture (not shown). The system is then sealed against leakage of respiration gases passing into the manifold ventilator port by sealing structure within the sputum trap 95. With the catheter 93 withdrawn, the knob 24 may be turned to closed condition. The luer collar 96 may then be turned to release the assembly 86 from its connection to the valved manifold 22. Aspiration/ventilation may then continue through the patient connection 50 and ventilation 40 ports.

As best shown by FIG. 5, an arrow 100 on the upper surface of the knob 24 indicates the open valve condition. FIG. 4 shows the valve 22 in its closed condition.

Reference in this disclosure to details of the illustrated or other preferred embodiments is not intended to limit the scope of the appended claims, which themselves recite those features regarded as important to the invention.

What is claimed is:

1. A valve for use in a patient ventilation/aspiration system, comprising:

a chamber, including first, second and third ports and a fluid path established between the first and third ports;

a valve comprising a stem positioned within said chamber, said stem being constructed and arranged for movement between a first position in which said stem blocks fluid flow through said second port;

a second position in which said stem provides a catheter travel pathway between said second and third ports, said catheter travel pathway comprising the fluid flow path throughout said third port;

actuation structure linked to said stem and operable to move said stem between said first and second positions; and said valve being further constructed and arranged to avoid blocking fluid flow between said first and third ports.

2. A valve according to claim 1, wherein said stem has a hollow center cavity opening towards said first port, said hollow center cavity being in open communication with said third port.

3. A valve according to claim 2, wherein said stem includes a slot transverse said hollow center cavity, said slot being positioned in registration with said third port when said stem is in either of said first or second positions.

4. A valve according to claim 3, wherein said stem includes:
   a wall with an outer surface in sealing relationship with said second port when said stem is in said first position; and
   an opening through said wall into said hollow center cavity, said opening being positioned and configured to register with said second port when said stem is in said second position.

5. An interface assembly for closed system endotracheal ventilating and aspirating procedures, comprising:
   a manifold having:
   a ventilation port in open communication with an interior chamber;
   a patient connection port in open communication with said interior chamber and forming a fluid flow path with said ventilation port, said patient connection port being out of registration with said ventilation port; and
   an access port in communication with said interior chamber and in registration with said patient connection port;
   said access port and patient connection port being positioned to provide a catheter travel pathway through said access port, said interior chamber and said patient connection port, said catheter travel pathway including that portion of the fluid flow path from said interior chamber throughout said patient connection port; and
   a valve, comprising:
      a stem positioned within said catheter travel pathway, and constructed and arranged for movement between a first position in which said stem blocks said catheter travel pathway, and a second position in which said stem provides a portion of said catheter travel pathway; and
      actuation structure linked to said stem and operable to move said stem between said first and second positions;
   said valve being further constructed and arranged to avoid blocking fluid flow between said ventilation port and said patient connection port.

6. An assembly according to claim 5, wherein said ventilation port is oriented generally transverse said catheter travel pathway.

7. An assembly according to claim 6, wherein said stem is positioned within said interior chamber.

8. An assembly according to claim 7, wherein said stem has a hollow center cavity opening towards said ventilation port, said hollow center cavity being in open communication with said patient connection port.

9. An assembly according to claim 8, wherein said stem includes a slot transverse said hollow center cavity, said slot being positioned in registration with said patient connection port when said stem is in either of said first or second positions.

10. An assembly according to claim 9, wherein said stem includes:
    a wall with an outer surface in sealing relationship with said access port when said stem is in said first position; and
    an opening through said wall into said hollow center cavity, said opening being positioned and configured to register with said access port when said stem is in said second position.

11. An assembly according to claim 5, including a connector comprising:
    a first part associated with said patient connection port and constituting a female portion comprising an inner cylindrical surface;
    a second part constituting a male portion comprising an outer cylindrical surface; and
    said first and second parts being structured and arranged to effect a plug fit connection capable of low friction rotation while maintaining a fluid tight seal at the interface between said first and second parts.

12. An assembly according to claim 11, wherein said first part is integral with said patient connection port.

13. An assembly according to claim 12, wherein said second part is structured as a conduit element, including a proximal end received by said first part and a distal end structured to couple with a patient intubation device.

14. An interface assembly for closed system endotracheal ventilating and aspirating procedures, comprising:
    a manifold having:
       a ventilation port in open communication with an interior chamber; a patient connection port in open communication with said interior chamber and forming a fluid flow path with said ventilation port, said patient connection port being out of registration with said ventilation port; and
       an access port in communication with said interior chamber and in registration with said patient connection port;
       said access port and patient connection port being positioned to provide a catheter travel pathway through said access port, said interior chamber and said patient connection port, said catheter travel pathway including that portion of the fluid flow path from said interior chamber throughout said patient connection port; and
    a valve, comprising:
       a stem positioned within said interior chamber constructed and arranged for movement between:
          a first position in which said stem blocks fluid flow through said access port; and
          a second position in which said stem provides a portion of said catheter travel pathway; and
       actuation structure linked to said stem and operable to move said stem between said first and second positions;
    said valve being further constructed and arranged to avoid blocking fluid flow between said ventilation port and said patient connection port.

15. An assembly according to claim 10, wherein said stem has a hollow center cavity opening towards said ventilation port, said hollow center cavity being in open communication with said patient connection port.

16. An assembly according to claim 15, wherein said stem includes a slot transverse said hollow center cavity, said slot being positioned in registration with said patient connection port when said stem is in either of said first or second positions.

17. An assembly according to claim 16, wherein said stem includes:
    a wall with an outer surface in sealing relationship with said access port when said stem is in said first position; and an opening through said wall into said hollow center cavity, said opening being positioned and configured to register with said access port when said stem is in said second position.

18. An assembly according to claim 14, including a connector comprising:
   a first part associated with said patient connection port and constituting a female portion comprising an inner cylindrical surface;
   a second part constituting a male portion comprising an outer cylindrical surface; and
   said first and second parts being structured and arranged to effect a plug fit connection capable of low friction rotation while maintaining a fluid tight seal at the interface between said first and second parts.

19. An assembly according to claim 18, wherein said first part is integral with said patient connection port.

20. An assembly according to claim 19, wherein said second part is structured as a conduit element, including a proximal end received by said first part and a distal end structured to couple with a patient intubation device.

* * * * *